US010058416B2

(12) United States Patent
Corbitt, Jr.

(10) Patent No.: US 10,058,416 B2
(45) Date of Patent: *Aug. 28, 2018

(54) TISSUE MARKING IMPLANT

(71) Applicant: SenoRx, Inc., Tempe, AZ (US)

(72) Inventor: John D. Corbitt, Jr., Lake Worth, FL (US)

(73) Assignee: SenoRx, Inc., Tempe, AZ (US)

(*) Notice: Subject to any disclaimer, the term of this patent is extended or adjusted under 35 U.S.C. 154(b) by 0 days.

This patent is subject to a terminal disclaimer.

(21) Appl. No.: 15/334,445

(22) Filed: Oct. 26, 2016

(65) Prior Publication Data
US 2017/0042664 A1 Feb. 16, 2017

Related U.S. Application Data

(60) Division of application No. 14/714,748, filed on May 18, 2015, now Pat. No. 9,480,554, which is a (Continued)

(51) Int. Cl.
A61F 2/12 (2006.01)
A61F 2/00 (2006.01)
A61L 27/18 (2006.01)
A61L 27/56 (2006.01)
A61L 27/58 (2006.01)
A61L 27/36 (2006.01)
A61B 90/00 (2016.01)

(52) U.S. Cl.
CPC ............ A61F 2/12 (2013.01); A61F 2/0059 (2013.01); A61F 2/0077 (2013.01); A61L 27/18 (2013.01); A61L 27/36 (2013.01); A61L 27/56 (2013.01); A61L 27/58 (2013.01); A61B 2090/3908 (2016.02); A61F 2210/0004 (2013.01); A61F 2210/0066 (2013.01)

(58) Field of Classification Search
CPC .......................................................... A61F 2/12
USPC .......................................................... 623/7-8
See application file for complete search history.

(56) References Cited

U.S. PATENT DOCUMENTS 2,899,362 A  8/1959  Sieger, Jr. et al.
3,005,457 A  10/1961  Millman
(Continued)

FOREIGN PATENT DOCUMENTS

EP    0255123 A2    2/1988
WO    9112823 A1    9/1991
(Continued)

OTHER PUBLICATIONS

Dewanjee et al., "Identification of New Collagen Formation with 125I-Labeled Antibody in Bovine Pericardial Tissue Valves Implanted in Calves", Nucl. Med. Biol. vol. 13, No. 4, pp. 413-422, 1986.
(Continued)

Primary Examiner — Suzette J Gherbi

(57) ABSTRACT

A prosthesis includes an outer capsule that is made of biosorbable material. An inner capsule is encapsulated by the outer capsule. A layer of fluid is interposed between the outer capsule and the inner capsule. In one implementation, the inner capsule surrounds autologous fluids or saline. Also, the layer of fluid interposed between the outer capsule and the inner capsule may comprise autologous fluids or saline.

11 Claims, 1 Drawing Sheet

Related U.S. Application Data continuation of application No. 14/166,328, filed on Jan. 28, 2014, now Pat. No. 9,039,763, which is a continuation of application No. 13/426,061, filed on Mar. 21, 2012, now Pat. No. 8,668,737, which is a continuation of application No. 12/965,405, filed on Dec. 10, 2010, now Pat. No. 8,157,862, which is a continuation of application No. 12/589,413, filed on Oct. 23, 2009, now Pat. No. 7,871,438, which is a division of application No. 11/108,785, filed on Apr. 19, 2005, now Pat. No. 7,637,948, which is a continuation-in-part of application No. 10/627,718, filed on Jul. 28, 2003, now Pat. No. 6,881,226, which is a division of application No. 09/828,806, filed on Apr. 10, 2001, now Pat. No. 6,638,308, which is a continuation-in-part of application No. 09/169,351, filed on Oct. 9, 1998, now Pat. No. 6,214,045.

(60) Provisional application No. 60/061,588, filed on Oct. 10, 1997, provisional application No. 60/077,639, filed on Mar. 11, 1998, provisional application No. 60/091,306, filed on Jun. 30, 1998.

(56) References Cited

U.S. PATENT DOCUMENTS

| | | | |
|---|---|---|---|
| 3,892,731 A | 7/1975 | Austin | |
| 3,921,632 A | 11/1975 | Bardani | |
| 4,005,699 A | 2/1977 | Bucalo | |
| 4,007,732 A | 2/1977 | Kvavle et al. | |
| 4,086,914 A | 5/1978 | Moore | |
| 4,197,846 A | 4/1980 | Bucalo | |
| 4,217,889 A | 8/1980 | Radovan et al. | |
| 4,298,998 A * | 11/1981 | Naficy | A61F 2/12 623/8 |
| 4,390,018 A | 6/1983 | Zukowski | |
| 4,428,082 A | 1/1984 | Naficy | |
| 4,438,253 A | 3/1984 | Casey et al. | |
| 4,442,843 A | 4/1984 | Rasor et al. | |
| 4,470,160 A | 9/1984 | Cavon | |
| 4,507,810 A * | 4/1985 | Bartholdson | A61F 2/12 623/8 |
| 4,582,640 A | 4/1986 | Smestad et al. | |
| 4,588,395 A | 5/1986 | Lemelson | |
| 4,661,103 A | 4/1987 | Harman | |
| 4,718,433 A | 1/1988 | Feinstein | |
| 4,740,208 A | 4/1988 | Cavon | |
| 4,762,128 A | 8/1988 | Rosenbluth | |
| 4,832,686 A | 5/1989 | Anderson | |
| 4,863,470 A | 9/1989 | Carter | |
| 4,938,763 A | 7/1990 | Dunn et al. | |
| 4,963,150 A | 10/1990 | Brauman | |
| 4,970,298 A | 11/1990 | Silver et al. | |
| 4,994,028 A | 2/1991 | Leonard et al. | |
| 5,013,090 A | 5/1991 | Matsuura | |
| 5,089,606 A | 2/1992 | Cole et al. | |
| 5,108,421 A | 4/1992 | Fowler | |
| 5,120,802 A | 6/1992 | Mares et al. | |
| 5,201,704 A | 4/1993 | Ray | |
| 5,289,831 A | 3/1994 | Bosley | |
| 5,320,100 A | 6/1994 | Herweck et al. | |
| 5,328,955 A | 7/1994 | Rhee et al. | |
| 5,360,416 A | 11/1994 | Ausherman et al. | |
| 5,366,756 A | 11/1994 | Chesterfield et al. | |
| 5,444,113 A | 8/1995 | Sinclair et al. | |
| 5,458,643 A | 10/1995 | Oka et al. | |
| 5,469,847 A | 11/1995 | Zinreich et al. | |
| 5,475,052 A | 12/1995 | Rhee et al. | |
| 5,499,989 A | 3/1996 | LaBash | |
| 5,507,807 A | 4/1996 | Shippert | |
| 5,508,021 A | 4/1996 | Grinstaff et al. | |
| 5,514,085 A | 5/1996 | Yoon | |
| 5,522,896 A * | 6/1996 | Prescott | A61B 17/0057 623/23.56 |
| 5,567,413 A | 10/1996 | Klaveness et al. | |
| RE35,391 E | 12/1996 | Brauman | |
| 5,599,552 A | 2/1997 | Dunn et al. | |
| 5,626,611 A | 5/1997 | Liu et al. | |
| 5,628,781 A | 5/1997 | Williams et al. | |
| 5,629,008 A | 5/1997 | Lee | |
| 5,676,146 A | 10/1997 | Scarborough | |
| 5,702,128 A | 12/1997 | Maxim et al. | |
| 5,702,682 A | 12/1997 | Thompson | |
| 5,702,716 A | 12/1997 | Dunn et al. | |
| 5,716,404 A | 2/1998 | Vacanti | |
| 5,716,981 A | 2/1998 | Hunter et al. | |
| 5,718,916 A | 2/1998 | Scherr | |
| 5,752,974 A | 5/1998 | Rhee et al. | |
| 5,782,775 A | 7/1998 | Milliman et al. | |
| 5,795,308 A | 8/1998 | Russin | |
| 5,808,007 A | 9/1998 | Lee et al. | |
| 5,820,918 A | 10/1998 | Ronan et al. | |
| 5,824,042 A | 10/1998 | Lombardi et al. | |
| 5,824,081 A * | 10/1998 | Knapp | A61F 2/12 623/23.72 |
| 5,840,777 A | 11/1998 | Eagles et al. | |
| 5,851,461 A | 12/1998 | Bakis et al. | |
| 5,853,366 A | 12/1998 | Dowlatshahi | |
| 5,869,080 A * | 2/1999 | McGregor | A61L 15/425 424/426 |
| 5,891,558 A | 4/1999 | Bell et al. | |
| 5,922,024 A * | 7/1999 | Janzen | A61F 2/12 623/8 |
| 5,941,890 A | 8/1999 | Voegele et al. | |
| 5,980,564 A | 11/1999 | Stinson | |
| 5,990,194 A | 11/1999 | Dunn et al. | |
| 6,027,471 A | 2/2000 | Fallon et al. | |
| 6,066,325 A | 5/2000 | Wallace et al. | |
| 6,090,996 A | 7/2000 | Li | |
| 6,159,240 A | 12/2000 | Sparer et al. | |
| 6,161,034 A | 12/2000 | Burbank et al. | |
| 6,162,192 A | 12/2000 | Cragg et al. | |
| 6,174,330 B1 | 1/2001 | Stinson | |
| 6,183,497 B1 | 2/2001 | Sing et al. | |
| 6,190,350 B1 | 2/2001 | Davis et al. | |
| 6,214,045 B1 * | 4/2001 | Corbitt, Jr. | A61F 2/12 424/400 |
| 6,224,630 B1 | 5/2001 | Bao et al. | |
| 6,231,615 B1 | 5/2001 | Preissman | |
| 6,270,464 B1 | 8/2001 | Fulton, III et al. | |
| 6,270,472 B1 | 8/2001 | Antaki et al. | |
| 6,280,514 B1 | 8/2001 | Lydzinski et al. | |
| 6,287,332 B1 | 9/2001 | Bolz et al. | |
| 6,316,522 B1 | 11/2001 | Loomis et al. | |
| 6,325,789 B1 | 12/2001 | Janzen et al. | |
| 6,333,029 B1 | 12/2001 | Vyakarnam et al. | |
| 6,347,241 B2 | 2/2002 | Burbank et al. | |
| 6,350,244 B1 | 2/2002 | Fisher | |
| 6,350,274 B1 | 2/2002 | Li | |
| 6,354,989 B1 | 3/2002 | Nudeshima | |
| 6,356,782 B1 | 3/2002 | Sirimanne et al. | |
| 6,371,904 B1 | 4/2002 | Sirimanne et al. | |
| 6,403,758 B1 | 6/2002 | Loomis | |
| 6,409,742 B1 | 6/2002 | Fulton, III et al. | |
| 6,427,081 B1 | 7/2002 | Burbank et al. | |
| 6,436,030 B2 | 8/2002 | Rehil | |
| 6,478,790 B2 | 11/2002 | Bardani | |
| 6,511,650 B1 | 1/2003 | Eiselt et al. | |
| 6,554,760 B2 | 4/2003 | Lamoureux et al. | |
| 6,567,689 B2 | 5/2003 | Burbank et al. | |
| 6,575,888 B2 | 6/2003 | Zamora et al. | |
| 6,575,991 B1 | 6/2003 | Chesbrough et al. | |
| 6,585,773 B1 | 7/2003 | Xie | |
| 6,628,982 B1 | 9/2003 | Thomas et al. | |
| 6,629,947 B1 | 10/2003 | Sahatjian et al. | |
| 6,638,308 B2 * | 10/2003 | Corbitt, Jr. | A61F 2/12 424/400 |
| 6,662,041 B2 | 12/2003 | Burbank et al. | |
| 6,666,893 B2 * | 12/2003 | Burg | A61F 2/0063 623/23.64 |
| 6,699,205 B2 | 3/2004 | Fulton, III et al. | |

(56) References Cited

U.S. PATENT DOCUMENTS

| | | |
|---|---|---|
| 6,716,444 B1 | 4/2004 | Castro et al. |
| 6,725,083 B1 | 4/2004 | Burbank et al. |
| 6,730,042 B2 | 5/2004 | Fulton et al. |
| 6,846,320 B2 | 1/2005 | Ashby et al. |
| 6,862,470 B2 | 3/2005 | Burbank et al. |
| 6,881,226 B2 | 4/2005 | Corbitt, Jr. et al. |
| 6,899,731 B2 | 5/2005 | Li et al. |
| 6,918,927 B2 | 7/2005 | Bates et al. |
| 6,993,375 B2 | 1/2006 | Burbank et al. |
| 6,996,433 B2 | 2/2006 | Burbank et al. |
| 7,047,063 B2 | 5/2006 | Burbank et al. |
| 7,056,957 B2 | 6/2006 | Omidian et al. |
| 7,070,722 B1 | 7/2006 | Gilchrist et al. |
| 7,160,258 B2 | 1/2007 | Imran et al. |
| 7,229,417 B2 | 6/2007 | Foerster et al. |
| 7,329,414 B2 | 2/2008 | Fisher et al. |
| 7,534,452 B2 | 5/2009 | Chernomorsky et al. |
| 7,565,191 B2 | 7/2009 | Burbank et al. |
| 7,637,948 B2 | 12/2009 | Corbitt, Jr. |
| 7,651,505 B2 | 1/2010 | Lubock et al. |
| 7,668,582 B2 | 2/2010 | Sirimanne et al. |
| 7,671,100 B2 | 3/2010 | Gaserod et al. |
| 7,783,336 B2 | 8/2010 | Macfarlane et al. |
| 7,792,569 B2 | 9/2010 | Burbank et al. |
| 7,871,438 B2 * | 1/2011 | Corbitt, Jr. ............... A61F 2/12 128/898 |
| 7,877,133 B2 | 1/2011 | Burbank et al. |
| 7,914,553 B2 | 3/2011 | Ferree |
| 7,983,734 B2 | 7/2011 | Jones et al. |
| 8,157,862 B2 | 4/2012 | Corbitt, Jr. |
| 8,177,792 B2 | 5/2012 | Lubock et al. |
| 8,306,602 B2 | 11/2012 | Sirimanne et al. |
| 8,320,993 B2 | 11/2012 | Sirimanne et al. |
| 8,320,994 B2 | 11/2012 | Sirimanne et al. |
| 8,361,082 B2 | 1/2013 | Jones et al. |
| 8,442,623 B2 | 5/2013 | Nicoson et al. |
| 8,626,269 B2 | 1/2014 | Jones et al. |
| 8,626,270 B2 | 1/2014 | Burbank et al. |
| 8,639,315 B2 | 1/2014 | Burbank et al. |
| 8,668,737 B2 * | 3/2014 | Corbitt, Jr. ............ A61F 2/0059 623/7 |
| 8,680,498 B2 | 3/2014 | Corbitt |
| 8,718,745 B2 | 5/2014 | Burbank et al. |
| 8,784,433 B2 | 7/2014 | Lubock et al. |
| 9,028,872 B2 | 5/2015 | Gaserod et al. |
| 9,039,763 B2 * | 5/2015 | Corbitt, Jr. ............ A61F 2/0059 623/7 |
| 9,237,937 B2 | 1/2016 | Burbank et al. |
| 9,480,554 B2 * | 11/2016 | Corbitt, Jr. ............ A61F 2/0059 |
| 2002/0010514 A1 * | 1/2002 | Burg ................ A61F 2/0063 623/23.75 |
| 2002/0022883 A1 | 2/2002 | Burg |
| 2002/0035324 A1 | 3/2002 | Sirimanne et al. |
| 2002/0082682 A1 | 6/2002 | Barclay et al. |
| 2002/0107437 A1 | 8/2002 | Sirimanne et al. |
| 2003/0036803 A1 | 2/2003 | McGhan |
| 2003/0236573 A1 | 12/2003 | Evans et al. |
| 2004/0101479 A1 | 5/2004 | Burbank et al. |
| 2004/0116802 A1 | 6/2004 | Jessop et al. |
| 2004/0204660 A1 | 10/2004 | Fulton et al. |
| 2004/0236212 A1 | 11/2004 | Jones et al. |
| 2004/0236213 A1 | 11/2004 | Jones et al. |
| 2005/0020916 A1 | 1/2005 | MacFarlane et al. |
| 2005/0033157 A1 | 2/2005 | Klien et al. |
| 2005/0033195 A1 | 2/2005 | Fulton et al. |
| 2005/0045192 A1 | 3/2005 | Fulton et al. |
| 2005/0059888 A1 | 3/2005 | Sirimanne et al. |
| 2005/0065354 A1 | 3/2005 | Roberts |
| 2005/0080337 A1 | 4/2005 | Sirimanne et al. |
| 2005/0080339 A1 | 4/2005 | Sirimanne et al. |
| 2005/0085724 A1 | 4/2005 | Sirimanne et al. |
| 2005/0100580 A1 | 5/2005 | Osborne et al. |
| 2005/0119562 A1 | 6/2005 | Jones et al. |
| 2005/0142161 A1 | 6/2005 | Freeman et al. |
| 2005/0175657 A1 | 8/2005 | Hunter et al. |
| 2005/0181007 A1 | 8/2005 | Hunter et al. |
| 2005/0187624 A1 | 8/2005 | Corbitt, Jr. |
| 2005/0208122 A1 | 9/2005 | Allen et al. |
| 2005/0234336 A1 | 10/2005 | Beckman et al. |
| 2006/0036159 A1 | 2/2006 | Sirimanne et al. |
| 2006/0079770 A1 | 4/2006 | Sirimanne et al. |
| 2006/0079805 A1 | 4/2006 | Miller et al. |
| 2006/0079829 A1 | 4/2006 | Fulton et al. |
| 2006/0122503 A1 | 6/2006 | Burbank et al. |
| 2006/0134185 A1 | 6/2006 | Odermatt et al. |
| 2006/0155190 A1 | 7/2006 | Burbank et al. |
| 2006/0173296 A1 | 8/2006 | Miller et al. |
| 2006/0177379 A1 | 8/2006 | Asgari |
| 2006/0235298 A1 | 10/2006 | Kotmel et al. |
| 2007/0135711 A1 | 6/2007 | Chernomorsky et al. |
| 2008/0091120 A1 | 4/2008 | Fisher |
| 2008/0097199 A1 | 4/2008 | Mullen |
| 2008/0188768 A1 | 8/2008 | Zarins et al. |
| 2009/0171198 A1 | 7/2009 | Jones et al. |
| 2009/0287078 A1 | 11/2009 | Burbank et al. |
| 2010/0010342 A1 | 1/2010 | Burbank et al. |
| 2010/0094169 A1 | 4/2010 | Lubock et al. |
| 2010/0121445 A1 | 5/2010 | Corbitt, Jr. |
| 2010/0298698 A1 | 11/2010 | Burbank et al. |
| 2010/0324416 A1 | 12/2010 | Burbank et al. |
| 2011/0082547 A1 | 4/2011 | Corbitt, Jr. |
| 2011/0092815 A1 | 4/2011 | Burbank et al. |
| 2011/0184280 A1 | 7/2011 | Jones et al. |
| 2012/0078092 A1 | 3/2012 | Jones et al. |
| 2012/0116215 A1 | 5/2012 | Jones et al. |
| 2012/0215230 A1 | 8/2012 | Lubock et al. |
| 2013/0144157 A1 | 6/2013 | Jones et al. |
| 2013/0281847 A1 | 10/2013 | Jones et al. |
| 2013/0310686 A1 | 11/2013 | Jones et al. |
| 2014/0094698 A1 | 4/2014 | Burbank et al. |
| 2014/0114186 A1 | 4/2014 | Burbank et al. |
| 2014/0243675 A1 | 8/2014 | Burbank et al. |
| 2015/0051477 A1 | 2/2015 | Jones et al. |
| 2015/0164610 A1 | 6/2015 | Field et al. |
| 2016/0120510 A1 | 5/2016 | Burbank et al. |
| 2016/0128797 A1 | 5/2016 | Burbank et al. |
| 2016/0199150 A1 | 7/2016 | Field et al. |
| 2017/0100203 A1 | 4/2017 | Field et al. |
| 2017/0119492 A1 | 5/2017 | Chesbrough et al. |

FOREIGN PATENT DOCUMENTS

| | | |
|---|---|---|
| WO | 9507057 A1 | 3/1995 |
| WO | 0170114 A1 | 9/2001 |
| WO | 0207786 A2 | 1/2002 |
| WO | 0241786 A2 | 5/2002 |
| WO | 2005089664 A1 | 9/2005 |
| WO | 2006012630 A2 | 2/2006 |
| WO | 2006097331 A2 | 9/2006 |
| WO | 2006105353 A2 | 10/2006 |
| WO | 2008073965 A2 | 6/2008 |
| WO | 2008077081 A2 | 6/2008 |

OTHER PUBLICATIONS

Ma, Jianbiao, et al. "A preliminary in vitro study on the fabrication and tissue engineering applications of a novel chitosan bilayer material as a scaffold of human neofetal dermal fibroblasts." 8iomaterials 22.4 (2001): 331-336.

Pignolet, Louis H., et al. "The alginate demonstration: Polymers, food science, and ion exchange." J. Chem. Educ 75.11 (1998): 1430.

Armstong, J.S., et al., "Differential marking of Excision Planes in Screened Breast lesions by Organically Coloured Gelatins", Journal of Clinical Pathology, Jul. 1990, No. 43 (7) pp. 604-607, XP000971447 abstract; tables 1,2.

Jong-Won Rhie, et al. "Implantation of Cultured Preadipocyte Using Chitosan/Alginate Sponge", Key Engineering Materials, Jul. 1, 2007, pp. 346-352, XP008159356, ISSN: 0252-1059, DOI: 10.4028/www.scientific.net/KEM.342-343.349, Department of Plastic Surgery, College of Medicine, The Catholic University of Korea, Seoul Korea.

(56) References Cited

OTHER PUBLICATIONS

Zmora, et al. (Tailoring the pore architecture in 3-D alginate scaffolds by controlling the freezing regime during fabrication, 2001, Elsevier Science Ltd.).
Madihally, et al. (Porous chitosan scaffolds for tissue engineering, 1998, Elsevier Science Ltd.).
Hyeong-Ho, et al. (Preparation of Macroporous Hydroxyapatite/ Chitosan-Alginate Composite Scaffolds for Bone Implants, 2007, Trans Tech Publications).

* cited by examiner

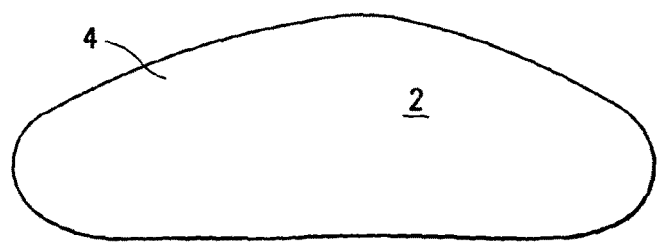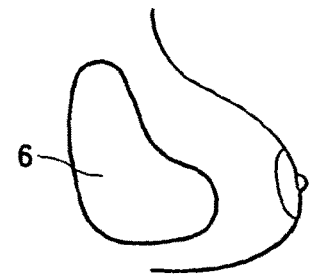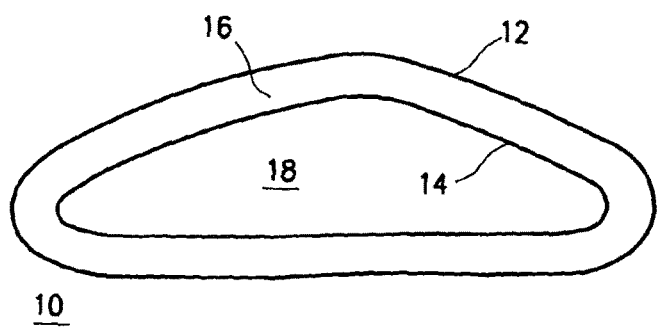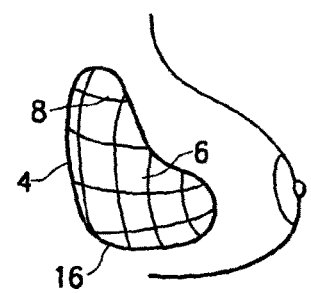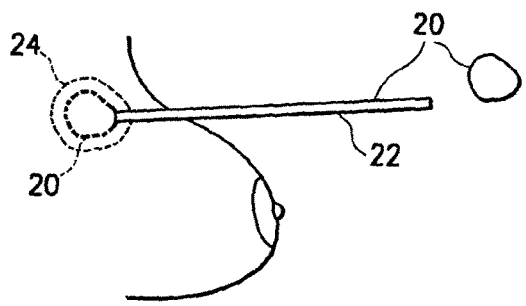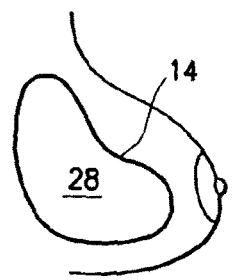

TISSUE MARKING IMPLANT

CROSS REFERENCE TO RELATED APPLICATIONS

This application is a division of application Ser. No. 14/714,748 filed May 18, 2015, now U.S. Pat. No. 9,480,554, which is a continuation of application Ser. No. 14/166,328 filed Jan. 28, 2014, now U.S. Pat. No. 9,039,763, which is a continuation of application Ser. No. 13/426,061, filed Mar. 21, 2012, now U.S. Pat. No. 8,668,737, which is a continuation of application Ser. No. 12/965,405, filed Dec. 10, 2010, now U.S. Pat. No. 8,157,862, which is a continuation of application Ser. No. 12/589,413, filed Oct. 23, 2009, now U.S. Pat. No. 7,871,438, which is a divisional of application Ser. No. 11/108,785, filed Apr. 19, 2005, now U.S. Pat. No. 7,637,948, which is a continuation-in-part of U.S. patent application Ser. No. 10/627,718, filed Jul. 28, 2003, now U.S. Pat. No. 6,881,226, which is a division of application Ser. No. 09/828,806, filed Apr. 10, 2001, now U.S. Pat. No. 6,638,308, which is a continuation-in-part of U.S. patent application Ser. No. 09/169,351, filed Oct. 9, 1998, now U.S. Pat. No. 6,214,045, which claims the benefit of U.S. Provisional Application Ser. No. 60/061,588, filed Oct. 10, 1997, U.S. Provisional Application Ser. No. 60/077,639, filed Mar. 11, 1998, and U.S. Provisional Application Ser. No. 60/091,306, filed Jun. 30, 1998, the disclosures of which are incorporated herein by reference.

BACKGROUND OF THE INVENTION

1. Field of the Invention

The present invention relates to implantable prostheses. More particularly, the present invention relates to implantable breast prostheses designed to eliminate encapsulation and reduce scarring, and to replace tissue removed for purposes of biopsy or lumpectomy.

2. Description of the Related Art

Breast prostheses are utilized for augmentation mammoplasty and in cosmetic surgery. Prostheses are also indicated in breast cancer surgery, such as lumpectomies, where a portion of the breast is removed and can leave some disfigurement if not replaced by a similar amount of tissue and/or augmentation material.

Similarly, biopsies can leave small dimples or imperfections if remedial steps are not taken. About 1 million breast biopsies are performed in the United States annually. As a result, some 200,000 new breast cancers are diagnosed each year.

Known methods of augmentation mammoplasty utilize silicone or saline implants. These methods have been complicated post-operatively by encapsulation of the implants, which can occur to varying degrees. Encapsulation produces a hard area of scar tissue around the implant, resulting in a rigid, abnormally-shaped mount beneath the breast tissue or *pectoralis* muscle, depending upon the placement of the implant.

Moreover, the known implant materials may not be indicated for replacement of smaller amounts of tissue, as would be required to prevent dimpling after biopsies, for example. Further, the known implant materials are not amenable to resizing. In addition, known implants are not capable of being implanted through a cannula or needle, and are not readily instilled with medicaments or chemical agents that would be useful in treating the patient.

Accordingly, a need exists for implants and methods that can be adapted for replacement of small as well as large amounts of tissue. A need also exists for implants that can be delivered through cannulae or needles, as well as being able to significantly reduce or eliminate encapsulation, resulting in a prolonged, aesthetically pleasing, soft mound below the breast tissue or *pectoralis* muscle. In addition, a need exists for implants into which useful substances, such as beneficial medications, chemical agents, hormonal treatments, stem cells, such as adipocytes, cellular precursors and components, and radiation media can be instilled to enhance the treatment capabilities of the implant in cancer and other breast pathology.

BRIEF SUMMARY OF THE INVENTION

The present invention overcomes deficiency of the prior art, such as those noted above, by providing an implant in which at least the outer portion of the implant, and as much as the entire implant, is made of a resorbable material. The implant is sized and shaped to reduce excised tissue. Preferably, the implant provides a support structure in the form of a framework or scaffold for the surrounding tissue after implantation. The support structure preferably is porous to permit the in-growth of fibrous replacement tissue. Advantageously, replacement tissue in-growth takes place without encapsulation and with reduced scarring.

The invention, in one form thereof, is directed to an implant for marking an area within a living body. The implant includes a matrix material and a marking material. The implant is formable to fit the shape and size of a cavity in the human body. The implant is configured to support tissue surrounding the cavity and to allow in-growth of fibrous tissue into and replace at least a portion of the matrix material.

The invention, in another form thereof, is directed to a tissue marking implant. The tissue marking implant includes a matrix and a dye marker. A matrix is collagen material. The matrix has a porous structure for supporting surrounding tissue of a breast and is configured to provide a framework for the in-growth of fibrous tissue into the matrix. The dye marker is supported by the matrix for dispersion into the tissue.

According to an embodiment of the invention, excised tissue is replaced by installing an implant having at least an outer shell of resorbable material. The implant is sized and shaped to replace the excised tissue. The implant supports surrounding tissue while fibrous tissue replaces the resorbable portion of the implant.

In a further development, at least a portion of the implant can be provided in the form of a compressible or non-compressible sponge or foam, or a self-expanding sponge or foam. The sponge or foam provides a porous support matrix for surrounding and in-growing tissue. In the form of a compressible, expandable, or self-expanding sponge or foam, the implant advantageously can be inserted through a cannula or a needle, or optionally can be directly inserted. Additionally, the implant can be instilled with beneficial materials, such as indicated medicaments, therapeutics, or diagnostic agents, as well as matrix enhancing additives.

Other features and advantages of the present invention will become apparent from the following description of the invention which refers to the accompanying drawings.

BRIEF DESCRIPTION OF THE DRAWINGS

FIG. 1 is a schematic elevation of a breast implant according to a preferred embodiment of the present invention.

FIG. 2 is a schematic sectional view of a breast after implantation of the implant of FIG. 1.

FIG. 3 is a schematic sectional view of a breast after implantation of an alternative embodiment of the implant of the present invention.

FIG. 4 is a schematic sectional view of a breast implant according to a second alternative embodiment of the present invention.

FIG. 5 is a schematic sectional view of a breast after implementation of the implant of FIG. 4.

FIG. 6 is a schematic sectional view of a breast implant and a method of insertion according to further alternative embodiments of the present invention, particularly for cases involving the removal of smaller pieces of tissue such as by biopsy and lumpectomy.

DETAILED DESCRIPTION OF THE INVENTION

Referring initially to FIGS. 1 and 2, an implant 2 has an outer shell 4 made of a biosorbable material woven into a mesh. The inner contents of the implant are fluids such as saline and autologous blood products.

Outer shell 4 is made entirely of biosorbable materials, such as collagens or polyglycolic acids, for example. Over a period of approximately three weeks to six months, the outer shell dissolves, leaving the inner contents 6 present inside the breast. Hard encapsulation will not occur because there is not a foreign body contained within the prosthetic space.

Referring to FIG. 3, implantation of an alternative embodiment of implant 2 is illustrated in which the outer shell 4 includes both biosorbable material, and nonabsorbable material, such as monofilament polypropylene fibers. Outer shell 4 is provided as a mesh or weave of the mixed material, surrounding contents 6 as described above. After a resorption period, contents 6 remain surrounded by a skeletal outer shell made up of non-absorbable fibers 8.

Advantageously, the proportions and spacing of the two types of materials can be altered to provide the desired properties of containment using a minimal amount of non-absorbable material. Accordingly, the non-absorbable fibers 8 which remain after the biosorbable materials resorb will act as a scaffolding to allow the prosthesis to hold its shape; however, because of the limited amount of foreign material, encapsulation and scarring are decreased.

Referring to FIGS. 4 and 5, a second alternative embodiment of the present invention is shown. A prosthesis 10 features two capsules, a larger, outer capsule 12 made of biosorbable materials, and a smaller inner capsule 14 made of a non-absorbable material. Inner capsule 14 also can be made partially resorbable as in the first alternative embodiment above. Outer capsule 12 and inner capsule 14 can be separated by a thin layer 16 of saline or autologous fluids such as those described above. Inner capsule 14 surrounds a more permanent member 18 made of autologous fluids or saline, for example.

After implantation, outer capsule 12 dissolves, thus preventing hardening by encapsulation of the prosthesis. The supply of fluid 16 between the capsules (a few to several c.c.'s) is absorbed by the body once released by the dissolution of outer capsule 12.

Referring to FIG. 6, a further alternative embodiment of the present invention includes an implant prosthesis 20 provided in the form of a matrix framework, such as a sponge or foam. The implant, which preferably is entirely biodegradable (resorbable), has a porous structure which supports the surrounding tissue and provides a framework for the in-growth of fibrous tissue material. FIG. 6 illustrates tissue portion 24 surrounding implant 20 into which marker dye included in the implant, and described further below, has leached over time from the implant, thereby marking the tissue. Accordingly, a surgeon performing a subsequent procedure easily will recognize the tissue surrounding the previous excision.

According to a preferred embodiment, the implant is provided in the form of a foam or sponge which can be modified by a surgeon prior to implantation, such as at a lumpectomy or biopsy site, simply by trimming the sponge to the appropriate size and shape. Alternatively, the implant can be a pre-shaped prosthesis of appropriate size, or an appropriate amount of foam or foam-forming materials. Optionally, the foam can be provided as a self-expanding matrix that either is compressed, or forms in situ. Advantageously, the implant can be modified to correspond to the breast tissue that either has been removed, requires replacement, or requires augmentation. The foam or sponge matrix is sufficiently resilient to support the surrounding tissue without collapsing.

A preferred embodiment of implantation is illustrated schematically in FIG. 6, whereby the implant is elastically compressible, and is delivered using a cannula or needle 22 inserted into the breast. A single implant 20 is shown being compressed so as to fit within cannula 22. A force is applied to drive the compressed implant distally through and out the distal end of the cannula into the implant site, where the resilient implant 20 expands to fill the implant site space.

The force for advancing the sponge or foam material through the cannula can be applied directly to the implant, or indirectly using fluids, for example. Advantageously, the implant can be used in conjunction with stereotactic biopsy instrumentation, such as the ABBI® System, the MIB System by US Surgical, or the Mammotome® System by Johnson and Johnson.

As a further alternative, the sponge or foam implant of the present invention can form all or part of a larger implant, such as those described above. Accordingly, the tissue supporting sponge or foam or foam matrix will form, for example, all or part of the outer shell 4 of implant 2. Implantation using open procedures usually would be indicated when the sponge implant of the present invention is used as all or part of a larger implant. Accordingly, the sponge or implant would be placed directly into the biopsy or lumpectomy cavity.

In addition, the implant 20 can be provided in the form of a self-expanding foam, which can be injected through a tubular member 22 such as a needle or cannula in a metered amount. An appropriate amount of foam-forming materials can be inserted through cannula 22 and allowed to expand or form a matrix within the cavity created by the excised tissue. Alternatively, a specialized, applicator may be used to inject the desired amount of the foam. The amount of foam is preselected to allow sufficient expansion to fill the void left by the excision and support the surrounding tissue to prevent dimpling.

Following insertion of the implant, such as by an open method or one of the stereotactic methods described above, the resorbable implant occupies the breast tissue cavity and supports the surrounding tissue until such time as it resorbs or biodegrades. After initial implantation, the patient's own fluids, fibroblast, and stem cells, such adipocytes, vascular stem cells, and others, permeates the sponge prosthesis. In the case of a small implant, such permeation would occur naturally, subsequent to implantation. In the case of a larger implant, providing the implant at least partially filled with fluids prior to implantation may be indicated.

Advantageously, the new prosthesis decreases encapsulation after implantation. Various biosorbable materials can be used in the implant of the present invention. Known biosorbable materials include polyglycolic acid (Dexon, Davis & Geck); polyglactin material (Vicryl, Ethicon); poliglecaprone (Monocryl, Ethicon); and synthetic absorbable lactomer 9-1 (Polysorb, United States Surgical Corporation)

Other foamable materials that can be utilized in the present invention include, without limitation, proteins such as collagen, fibronectin, laminin and fibrin, most preferably collagen, and high molecular weight polysaccharides, such as heparan sulphate, chondroitin sulphate, hyaluronic acid and dermatan sulphate. Mixtures of any of the aforementioned materials also can be used, as required.

The materials can be modified, by cross-linking for example, to control degradation rates over varying lengths of time, after which they are substantially or completely resorbed.

Foams can be formed by various means known to those skilled in the art, including injecting an aerosol into a gel, and freeze-drying aqueous dispersions of the foam-forming material. Foaming agents can be included to promote formation of the foam. In addition, stabilizing agents can be included to enhance foam stability. The foams can be extruded or formed in situ.

According to the present invention, these products may be mixed with one another or combined to provide various resorption times or gradients, and/or may be interrelated with non-absorbable materials, such as polypropylene or PTFE (polytetrafluoroethylene) sold as (Gore-Tex®) material, for example. In an instance where a non-absorbable material is utilized, the non-resorbable implant section will remain partially intact as a permanent structure.

In each of the embodiment, the resorbable portions of the prosthesis ultimately biodegrades, and the patient is left with autologous tissue, some of which may have been implanted, or a permanent implant such as saline, as a filler for the biopsy cavity, thus preserving the contour of the breast and preventing indentation of the overlying skin.

The implants of the present invention further can be instilled, before or after implantation, with indicated medicines and other chemical or diagnostic agents. Examples of such agents include, but are not limited to, antibiotics, chemotherapies, other cancer therapies, brachytherapeutic material for local radiation effect, x-ray opaque or metallic material for identification of the area, hemostatic material for control of bleeding, growth factor hormones, immune system factors, gene therapies, biochemical indicators or vectors, and other types of therapeutic or diagnostic materials which may enhance the treatment of the patient.

The breast implant preferably includes a permanent or temporary dye marker such as, but not limited to, indigo carmine or methylene blue. This marker serves as a visual identification of the area that has been biopsied or a lumpectomy has been performed so that in the future an operating surgeon can identify the surrounding tissue before he violates the previously biopsied cavity. These dyes leach into the breast tissue giving the surgeon an indication when he is nearing the point of interest, that being a previous biopsy site particularly if it is positive for a cancer or if it is a site for which a lumpectomy has been previously performed and the pathologist advises us that there is residual cancer. The surgeon can thus remove any of the surrounding breast tissue that contains dye and depending upon its concentration and the distance that it has traveled from the biopsy site will give us an indication of how much tissue should appropriately be removed.

This dye may be integrated with a bioabsorbable material such as, but not limited to collagen or may be in a separate capsule that is inserted with the bioabsorbable material as well as a metallic device for radiographic identification.

These two dyes are very dark colored dyes and these do leach through the breast tissue but will not stain the overlying skin.

The present invention has been described particularly in connection with a breast implant, but it will be obvious to those of skill in the art that the invention can have application to other parts of the body, such as the face, and generally to other soft tissue or bone. Accordingly, the invention is applicable to replacing missing or damaged soft tissue, structural tissue or bone, or for cosmetic tissue or bone replacement.

Although the present invention has been described in relation to particular embodiments thereof, many other variations and modifications and other uses will become apparent to those skilled in the art. It is preferred, therefore, that the present invention be limited not only by the specific disclosure herein, but only by the appended claims.

What is claimed is:

1. A prosthesis, comprising:
   an outer capsule made of biosorbable material;
   an inner capsule encapsulated by the outer capsule, wherein the inner capsule surrounds a member made of autologous fluids; and
   a layer of fluid interposed between the outer capsule and the inner capsule.

2. The prosthesis of claim 1, wherein the inner capsule is partially resorbable.

3. The prosthesis of claim 1, wherein the autologous fluids are autologous blood products.

4. The prosthesis of claim 1, wherein the layer of fluid interposed between the outer capsule and the inner capsule comprises autologous fluids.

5. The prosthesis of claim 4, wherein the autologous fluids are autologous blood products.

6. A prosthesis for insertion into a surgically formed cavity, comprising:
   an inner capsule containing a fluid;
   an outer capsule made of biosorbable material, the outer capsule encapsulating the inner capsule; and
   a fluid layer that separates the inner capsule and the outer capsule, wherein the fluid layer comprises autologous fluids.

7. The prosthesis of claim 6, wherein the inner capsule is partially resorbable.

8. The prosthesis of claim 6, wherein the fluid contained by the inner capsule is autologous fluids.

9. The prosthesis of claim 6, wherein the fluid contained by the inner capsule is saline.

10. The prosthesis of claim 8, wherein the autologous fluids are autologous blood products.

11. A prosthesis for insertion into a surgically formed cavity, comprising:
    an inner capsule containing a fluid;
    an outer capsule made of biosorbable material, the outer capsule encapsulating the inner capsule; and
    a fluid layer that separates the inner capsule and the outer capsule, wherein the fluid layer comprises autologous blood products.

* * * * *